United States Patent
Müller et al.

(10) Patent No.: US 9,150,912 B2
(45) Date of Patent: Oct. 6, 2015

(54) OLIGONUCLEOTIDES COMPRISING A LABEL ASSOCIATED THROUGH A LINKER

(75) Inventors: Daniel Müller, Hilden (DE); Francesca Di Pasquale, Hilden (DE)

(73) Assignee: QIAGEN GMBH, Hilden (DE)

(*) Notice: Subject to any disclaimer, the term of this patent is extended or adjusted under 35 U.S.C. 154(b) by 0 days.

(21) Appl. No.: 14/115,785

(22) PCT Filed: May 4, 2012

(86) PCT No.: PCT/EP2012/058277
§ 371 (c)(1),
(2), (4) Date: Dec. 16, 2013

(87) PCT Pub. No.: WO2012/152708
PCT Pub. Date: Nov. 15, 2012

(65) Prior Publication Data
US 2014/0178878 A1 Jun. 26, 2014

(30) Foreign Application Priority Data
May 6, 2011 (EP) ..................................... 11165133

(51) Int. Cl.
C07H 17/00 (2006.01)
C07H 21/02 (2006.01)
C07H 21/04 (2006.01)
C07H 19/04 (2006.01)
C12Q 1/68 (2006.01)
B01L 3/00 (2006.01)
C07H 21/00 (2006.01)

(52) U.S. Cl.
CPC .............. *C12Q 1/6853* (2013.01); *C07H 21/00* (2013.01); *C12Q 1/686* (2013.01); *C12Q 1/6813* (2013.01); *C12Q 1/6876* (2013.01); *C12Q 2525/197* (2013.01); *C12Q 2563/107* (2013.01)

(58) Field of Classification Search
CPC .............. C12Q 1/6853; C12Q 1/6876; C12Q 2525/197; C12Q 2563/107; C07H 21/00
USPC ........ 536/4.1, 23.1, 24.3, 26.5, 26.6; 435/6.1, 435/91.1; 422/430
See application file for complete search history.

(56) References Cited

U.S. PATENT DOCUMENTS

| 5,721,355 A | 2/1998 | Brush |
| 8,304,191 B2 * | 11/2012 | Eid et al. ..................... 435/6.11 |
| 2005/0272053 A1 | 12/2005 | Mao et al. |

FOREIGN PATENT DOCUMENTS

| WO | WO 95/19449 A1 | 7/1995 |
| WO | WO 01/83502 A1 | 11/2001 |
| WO | WO2007/015168 | * 2/2007 |

OTHER PUBLICATIONS

Stratagene Catalog 1988, p. 39.*
Seelig, et al., "Site-Specific Modification of Enzymatically Synthesized RNA: Transcription initiation and Diels-Alder Reaction", Tetrahedron Letters, vol. 38, No. 44, Jan. 1, 1997, pp. 7729-7732, XP002541671.
Dapprich, et al., "Base-dependent pyrene fluorescence used for in-solution detection of nucleicacids", Journal of Fluorescence, vol. 7, Jan. 1, 1997, pp. 87-89, XP009097069.
Akinori et al., "Dethreading of Deoxyribonucleotides through [alpha]-Cyclodextrin", Chemistry—An Asian Journal, Vol, 5, No. 10, Oct. 4, 2010, pp. 2177-2180, XP055008968.
Richardson, et al., "Tethered oligonucleotide probes. A strategy for the recognition of structured RNA", Journal of the American Chemical Society, vol. 113, No. 13, Jun. 1, 1991, pp. 5109-5111, XP055008991.
Mouscadet, et al., "Triple Helix Formation with Short Oligonucleotide-Intercalator Conjugates Matching the HIV-1 U3 LTR End Sequence", Biochemistry, vol. 33, No. 14, Apr. 1, 1994, pp. 4187-4196, XP055008784.
Berti, "Energy Transfer Cassettes for Facile Labeling of Sequencing and PCR Primers", Analytical Biochemistry, vol. 292, No. 2, May 15, 2001, pp. 188-197, XP055008783.

* cited by examiner

*Primary Examiner* — Jezia Riley
(74) *Attorney, Agent, or Firm* — Fanelli Haag PLLC

(57) ABSTRACT

The present application discloses a labeled nucleotide comprising a label attached via a linker, wherein said labeled nucleotide has the formula wherein $R^1$ is a residue with a negative net charge, preferably selected from the group consisting of a phosphate group, and a sulphate group; wherein $R^2$, $R^3$ and $R^4$ are independently selected from the group consisting of $H_2$, $OH_2$, and O; wherein "n" is an integer between 0 and 16; wherein "a" is an integer between 1 and 10; wherein SP is absent or a spacer; wherein X is said label; and wherein Y is a nucleotide or nucleoside. Furthermore, oligonucleotides comprising a labeled nucleotide according to the present invention and the use as a primer in amplification based methods is disclosed herein.

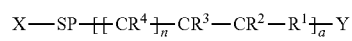

20 Claims, 1 Drawing Sheet

OLIGONUCLEOTIDES COMPRISING A LABEL ASSOCIATED THROUGH A LINKER

Figure 1:
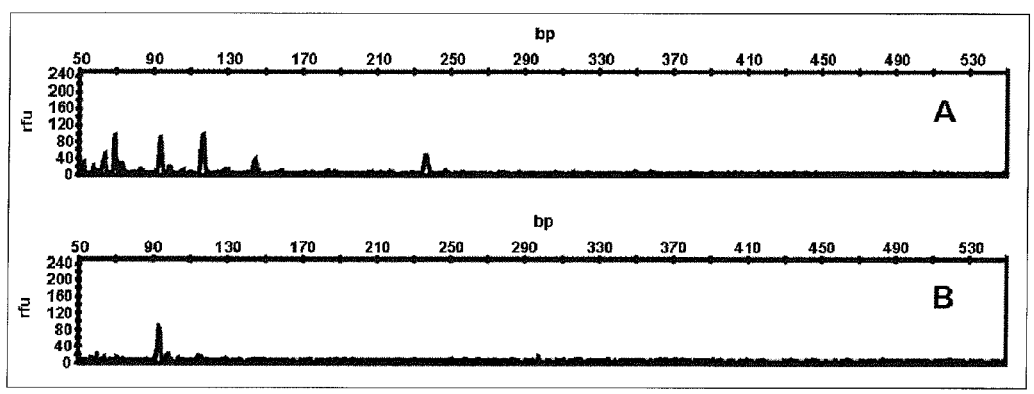

This application is a National Stage of PCT/EP2012/055277, filed May 4, 2012 which claims priority to European Application No, 11165133.7, filed May 6, 2011, the disclosures of which are incorporated herein by reference in their entirety.

FIELD OF THE INVENTION

The present invention is in the field of biology, more particularly in the field of molecular biology. More specifically, it is in the field of nucleic acid amplification and detection of preferable RNA and DNA molecules.

The instant application contains a Sequence Listing which has been submitted in ASCII format via EFS-Web and is hereby incorporated by reference in its entirety. Said ASCII copy, created on Nov. 4, 2013, is named 0051_0081US1_Sequence_Listing.txt and is 1855 bytes in size.

BACKGROUND OF THE INVENTION

Nowadays, amplification and detection of nucleic acids such as DNA is used in different approaches. In many routine diagnostics the analysis of the amplified nucleic acids is conducted via capillary electrophoresis. This method separates the analytes according to the length of the DNA molecules and detects them via fluorescent labels. In the resulting electropherograms peaks identify DNA molecules of a certain lengths. However, due to artefacts, such as degraded products or primers, small peaks above the baseline (background peaks) appear resulting in a loss of sensitivity. These background peaks represent free fluorescent labels and/or short oligonucleotides (1 to 8 bases) comprising the labels.

One problem underlying the present invention is to provide labeled oligonucleotides with an increased stability to reduce the background peaks and to increase sensitivity of detection.

DESCRIPTION OF THE PRESENT INVENTION

The inventors unexpectedly found that the use of an oligonucleotide as a primer, wherein said oligonucleotide comprises a nucleotide attached to a label via a C-linker comprising a negative charged residue as disclosed herein below, reduces background peaks in the analysis of the amplification products. Hence, the present invention relates to a labeled nucleotide comprising a label attached by a linker, wherein the labeled nucleotide has the formula

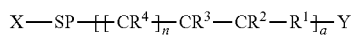  Formula 1 wherein $R^1$ is a residue with a negative net charge, preferably selected from the group consisting of a phosphate group, and a sulphate group;
wherein $R^2$, $R^3$ and $R^4$ are independently selected from the group consisting of $H_2$, $OH_2$, and O;
wherein n is an integer between 0 and 16;
wherein "a" is an integer between 1 and 10;
wherein SP is absent or a spacer;
wherein X is said label; and
wherein Y is a nucleotide or nucleoside.

The present invention further relates to an oligonucleotide comprising at least one labeled nucleotide according to the present invention.

Furthermore, the present invention relates to a kit comprising an oligonucleotide comprising a labeled nucleotide according to the present invention.

The invention also relates to the use of an oligonucleotide according to the present invention as a primer in a nucleic acid amplification method. Furthermore, the invention relates to the use of an oligonucleotide according to the present invention as a hybridization probe.

Detailed Description of the Present Invention

The labeled nucleotide according to the present invention comprises a label attached by a linker, wherein said labeled nucleotide has the formula

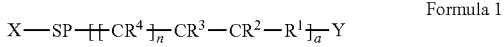  Formula 1 as outlined above. However, preferred embodiments are described in the following.

In a preferred embodiment of the present invention $R^1$ is a phosphate group.

The inventors found that by increasing the numbers of repeats (represented by "a") the diminishing of dye blobs in electropherograms is increased. However, the skilled person will recognize that increasing the number of $C_3$-repeats also increases the costs of the labeled nucleotide or oligonucleotide. Hence, in one embodiment of the present invention "a" is selected from the group of 1, 2, 3, 4, 5, 6, 7, 8, 9 and 10. The inventors unexpectedly found that a number of two repeats confers good properties with respect to stability of the oligonucleotide and amplification products. Hence, in a preferred embodiment of the present invention "a" is selected from the group of 1, 2 and 3, preferably "a" is 2.

In one embodiment of the present invention n is 1, $R^2$, $R^3$, and $R^4$ are each $H_2$, and $R^1$ is a phosphate group; and "a" is 2.

The length of the repeats may be varied according the needs. Hence, in one embodiment of the present invention n is an integer between 0 and 16. However, the inventors unexpectedly found that a repeat length of 3 does show particularly good properties. Hence, in one embodiment of the present invention n is 1. In this case the labeled nucleotide has the formula:

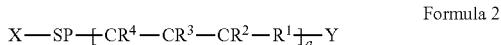  Formula 2 wherein $R^1$ is a residue with a negative net charge, preferably selected from the group consisting of a phosphate group, and a sulphate group;
wherein $R^2$, $R^3$ and $R^4$ are independently selected from the group consisting of $H_2$, $OH_2$, and O;
wherein "a" is an integer between 1 and 10;
wherein SP is absent or a spacer;
wherein X is said label; and
wherein Y is a nucleotide or nucleoside.

All embodiments disclosed herein, which are applicable to Formula 1, i.e. excluding the embodiments concerning "n", apply also to Formula 2. However, in one embodiment of Formula 2 $R^2$, $R^3$, and $R^4$ are each $H_2$, and $R^1$ is a phosphate group; and "a" is 2.

In one embodiment X is selected from the group of labels consisting of fluorophores, chromophores, radioisotopes, chemiluminescence and enzymes. In a preferred embodiment X is a fluorophore, preferably selected from the group of fluorophores comprising 5- or 6-carboxyfluorescein (FAM™), VIC™, NED™, fluorescein, fluorescein isothiocyanate (FITC), IRD-700/800, cyanine dyes, such as CY3™, CY5™, CY3.5™, CY5.5™, Cy7™, xanthen, 6-carboxy-2',4',7',4,7-hexachlorofluorescein (HEX), 6-carboxy-1,4-dichloro-2',7'-dichloro-fluorescein (TET®), 6-carboxy-4',5'-dichloro-2',7'-dimethodyfluorescein (JOE™), N,N,N',N'-tetramethyl-6-carboxyrhodamine (TAMRA™), 6-carboxy-X-rhodamine (ROX), 5-carboxyrhodamine-6G (R6G5), 6-carboxyrhodamine-6G (RG6), rhodamine, rhodamine green, rhodamine red, rhodamine 110, Rhodamin 6G®, BODIPY dyes, such as BODIPY TMR, oregon green, coumarines, such as umbelliferone, benzimides, such as Hoechst 33258; phenanthridines, such as Texas Red®, California Red®, Yakima Yellow, Alexa Fluor® 350, Alexa Fluor® 405, Alexa Fluor® 430, Alexa Fluor® 488, Alexa Fluor® 500, Alexa Fluor® 514, Alexa Fluor®532, Alexa Fluor® 546, Alexa Fluor® 555, Alexa Fluor® 568, Alexa Fluor® 594, Alexa Fluor® 610, Alexa Fluor® 633, Alexa Fluor® 647, Alexa Fluor® 660, Alexa Fluor® 680, Alexa Fluor® 700, Alexa Fluor® 750, PET®, ethidium bromide, acridinium dyes, carbazol dyes, phenoxazine dyes, porphyrine dyes, polymethin dyes, Atto 390, Atto 425, Atto 465, Atto 488, Atto 495, Atto 520, Atto 532, Atto 550, Atto 565, Atto 590, Atto 594, Atto 620, Atto 633, Atto 647N, Atto 655, Atto RhoG6, Atto Rho11, Atto Rho12, Atto Rho101, BMN™-5, BMN™-6, CEQ8000 D2, CEQ8000 D3, CEQ8000 D4, DY-480XL, DY-485XL, DY-495, DY-505, DY-510XL, DY-521XL, DY-521XL, DY-530, DY-547, DY-550, DY-555, DY-610, DY-615, DY-630, DY-631, DY-633, DY-635, DY-647, DY-651, DY-675, DY-676, DY-680, DY-681, DY-700, DY-701, DY-730, DY-731, DY-732, DY-750, DY-751, DY-776, DY-780, DY-781, DY-782, 6-carboxy-4',5'-dichloro-2',7'-dimethoxyfluorescein (JOE), TET™, CAL Fluor® Gold 540, CAL Fluor RED 590, CAL Fluor Red 610, CAL Fluor Red 635, IRDye® 700Dx, IRDye® 800CW, Marina Blue®, Pacific Blue®, Yakima Yellow®, 6-(4,7-Dichloro-2',7'-diphenyl-3',6'-dipivaloylfluorescein-6-carboxamido)-hexyl-1-O-(2-cyanoethyl)-(N,N-diisopropyl)-phosphoramidite (SIMA), CAL Fluor® Gold 540, CAL Fluor® Orange 560, CAL Fluor Red 635, Quasar 570, Quasar 670, LIZ, Sunnyvale Red, LC Red® 610, LC Red® 640, LC Red®670, and LC Red® 705. In a further preferred embodiment of the present invention, X is selected from the group of fluorophores consisting of Atto 465, DY-485XL, FAM™, Alexa Fluor® 488, DY-495, Atto 495, DY-510XL, JOE, TET™, CAL Fluor® Gold 540, DY-521XL, Rhodamin 6G®, Yakima Yellow®, Atto 532, Alexa Fluor®532, HEX, SIMA, Atto RhoG6, VIC, CAL Fluor Orange 560, DY-530, TAMRA™, Quasar 570, Cy3™, NED™, DY-550, Atto 550, Alexa Fluor® 555, PETS, CAL Fluor RED 590, ROX, Texas Red®, CAL Fluor Red 610, CAL Fluor Red 635, Atto 633, Alexa Fluor® 633, DY-630, DY-633, DY-631, LIZ, Quasar 670, DY-635, and Cy5™. In a yet further preferred embodiment X is selected from group of fluorophores consisting of FAM™, DY-510XL, DY-530, and Atto 550. In a yet further preferred embodiment of the present invention n is 1, $R^2$, $R^3$, and $R^4$ are each $H_2$, and $R^1$ is a phosphate group; a is 2; and X is selected from the group of fluorophores consisting of Atto 465, DY-485XL, FAM™, Alexa Fluor® 488, DY-495, Atto 495, DY-510XL, JOE, TET™, CAL Fluor® Gold 540, DY-521XL, Rhodamin 6G®, Yakima Yellow®, Atto 532, Alexa Fluor®532, HEX, SIMA, Atto RhoG6, VIC, CAL Fluor Orange 560, DY-530, TAMRA™, Quasar 570, Cy3™, NED™, DY-550, Atto 550, Alexa Fluor® 555, PET®, CAL Fluor RED 590, ROX, Texas Red®, CAL Fluor Red 610, CAL Fluor Red 635, Atto 633, Alexa Fluor® 633, DY-630, DY-633, DY-631, LIZ, Quasar 670, DY-635, and Cy5™ In an even more preferred embodiment of the present invention n is 1, $R^2$, $R^3$, and $R^4$ are each $H_2$, and $R^1$ is a phosphate group; a is 2; and X is selected from the group of fluorophores consisting of FAM™, DY-510XL, DY-530, and Atto 550.

Furthermore, the linker may comprise a spacer (SP) as known from the prior art. In context of the present invention the linker is attached to $CR^4$ or $CR^3$, respectively, via a phosphate group ($PO_4$). For example a $C_5$-spacer or a $C_6$-spacer may be used between the label and the linker according to the present invention, preferably the spacer is a branched or unbranched aminolinker. In a further preferred embodiment the spacer is selected from the group of $C_2$- to $C_{18}$-spacer, preferably the spacer is from the group of $C_3$-spacer to $C_{12}$-spacer. In a very special embodiment the spacer is a $C_5$-spacer or a $C_6$-spacer. In a preferred embodiment of the present invention n is 1, $R^2$, $R^3$, and $R^4$ are each $H_2$, and $R^1$ is a phosphate group; and a is 2 and X is selected from the group of fluorophores consisting of FAM™, DY-510XL, DY-530, and Atto 550, wherein X comprises a spacer between the fluorophore and the linker, preferably from the group of $C_2$ to $C_{18}$-spacer, more preferably from the group of $C_3$ or $C_{12}$-spacer, even more preferably a $C_5$-spacer or a $C_6$-spacer, preferably a $C_5$ or a $C_6$ aminolinker.

Aminolinker in context of the present invention refers in general to a carbon chain having 1 to 30 carbons or polyethylene glycol presented by $(CH2CH2O)_n$ (n=2 to 400). They may be branched or unbranched. Amino Linker may be used to incorporate a primary amino group onto the 5'-end, the 3'-end, the exocyclic amino group or a modified 2'-position of an oligonucleotide. The active amino group may be used for labeling oligonucleotides using labeling agents, e.g. in the form of N-hydroxy succinimide ester.

The term "nucleotide" in context with the present invention relates to a nucleobase (nitrogenous base) linked to a 5'-carbon sugar (either ribose or 2'-deoxyribose) and 1 to 3 phosphate groups. The nucleobase and the 5-carbon sugar form the nucleoside. The phosphate groups may be bond either to the 2'-, the 3'- or the 5'-carbon of the sugar. However, in a preferred embodiment the phosphate group is bond to the 5'-carbon. Unless stated otherwise, nucleotide in context of the present invention refers to a nucleoside with the phosphate group at the 5'-carbon of the sugar. In a preferred embodiment the nucleotide is selected from the group of monophosphate nucleosides, diphosphate nucleosides and triphosphate nucleosides. In a preferred embodiment the nucleotide is selected from the group of purine nucleotides and pyrimidine nucleotides, preferably selected from the group consisting of adenine nucleotides, thymidine nucleotides, cytosine nucleotides, guanine nucleotides, uridine nucleotides, and inosine nucleotides. Modified nucleotide bases are also encompassed, wherein the nucleotide bases are for example hypoxanthine, xanthine, 7-methylguanine, xanthinosine, 7-methylguanosine, 5,6-dihydrouracil, 5-methylcytosine, pseudouridine, dihydrouridine, 5-methylcytidine. Furthermore, ddNTPS of the above described molecules are encompassed in the present invention.

The skilled artisan will recognize that for the use in subsequent chemical reactions or for storage purposes, it may be desirable to protect the nucleotide according to the present invention. Hence, in one embodiment of the present invention the labeled nucleotide further comprises a protecting group. Protecting groups are known by those skilled in the art. They may for example be selected from the group consisting of dimethoxytrityl, 5'-O-(α-methyl-6-nitropiperonyloxycarbonyl), trifluoroacetyl, monomethoxytrityl, methoxymethyl ether, β-methoxyethoxymethyl ether, methylthiomethyl ether, pivaloyl, tetrahydropyranyl, 9-fluorenylmethyloxycarbonyl, acetyl, benzoyl, isobutyryl, p-methoxyphenyl, tosyl e.g. for the protection of the 5'-hydroxyl group or amino groups; benzoyl, benzyl, isobutyryl, acetyl, phenoxyacety, 4-isopropylphenoxyacetyl, dimethylformamide e.g. for the protection of exocyclic amino groups; 2-cyanoethyl and methyl e.g. for the protection of phosphate and phosphite groups; t-butyldimethylsilyl or t-butyldimethylsilyloxymethyl e.g. for the protection of the 2'-hydroxy group.

The inventors unexpectedly found that a labeled nucleotide according to the present invention incorporated into oligonucleotides results in an increased stability of the oligonucleotide. Furthermore, when using said oligonucleotide as a primer for amplifying nucleic acids the stability of the amplification products was greatly enhanced. Hence, the present invention also relates to an oligonucleotide comprising at least one labeled nucleotide according to the present invention. The skilled artisan will recognize that the labeled nucleotide according to the present invention may be located at different positions of an oligonucleotide, for example, at the 5'-end or at an internal position of the oligonucleotide. If the oligonucleotide according to the present invention is used as a hybridization probe the labeled nucleotide according to the present invention may also be present at the 3'-end of the oligonucleotide. However, in a preferred embodiment of the oligonucleotide according to the present invention the labeled nucleotide according to the present invention is located at the 5'-end of the oligonucleotide. It will be readily understood by the skilled person, that the linker according to the present invention may be attached to the carbons of the sugar of the nucleotide or it may be attached to the nucleobase. In one embodiment of the present invention the linker is attached to the nucleobase of the nucleotide, preferably to the exocyclic amino group of the nucleobase. In a preferred embodiment of the present invention the linker is attached to the 5'-carbon of the sugar. In a more preferred embodiment of the present invention $R^1$ is a phosphate group and Y is the 5'-carbon of the carbon of the nucleoside.

In an especially preferred embodiment of the present invention n is 1, $R^2$, $R^3$, and $R^4$ are each $H_2$, and $R^1$ is a phosphate group; "a" is 2 and X is selected from the group of fluorophores consisting of FAM™, DY-510XL, DY-530, and Atto 550, wherein SP is a $C_2$ to $C_{18}$-spacer, more preferably a $C_3$ to $C_{12}$-spacer even more preferably a $C_5$ or $C_6$-spacer, yet more preferably a $C_6$-spacer and wherein Y is the 5'-carbon of the sugar of a nucleoside.

Methods to link nucleotides or oligonucleotides to labels are known by the person skilled in the art. He may for example commercially order the desired linkers, i.e. the single repeating units, e.g. C3-linkers, by known commercial suppliers, such as GlenResearch or Berry and link them to the nucleotide or nucleoside and the label or spacer, respectively. However, the skilled artisan is furthermore aware of methods to produce the linkers. The skilled artisan for example knows methods to produce phosphoramidites containing various protecting groups (DMTr, TBDMS, Lev) (e.g. C3-Phosphoramidite; (3-(4,4'-Dimethoxytrityloxy)propyl-1-[(2-cyanoethyl)-(N,N-diisopropyl)]-phosphoramidite) which can then be used as linkers (see for example Su Jeong Kim et al. "Synthesis of Novel Phosphoramidite Building Blocks from Pentaerythritol"; Synlett 2003, No. 12; DOI: 10.1055/s-2003-41406).

The skilled artisan will recognize that the oligonucleotide according to the present invention is suited for different applications. It may be desirable that the oligonucleotide according to the present invention comprises more than one labeled nucleotide according to the present invention. In one embodiment the oligonucleotide comprises 1 to 4 labeled nucleotides according to the present invention, preferably 1 to 3 labeled nucleotides according to the present invention, more preferably 1 or 2 labeled nucleotides according to the present invention, even more preferably 1 labeled nucleotide according to the present invention.

An "internal position" in context of the present invention means that the labeled nucleotide according to the present invention is not at the 5'- or 3'-end of the oligonucleotide according to the present invention. If the labeled nucleotide according to the present invention is present at an internal position of the oligonucleotide it may be desirable that the position has a minimal distance to the 3'-end and/or 5'-end. In a preferred embodiment of the present invention the oligonucleotide according to the present invention has the following sequence:

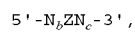

$$5'-N_bZN_c-3',$$

wherein N may be any nucleotide,
wherein "b" and "c" represent the number of nucleotides and may range from 1 to 150, preferably between 3 and 50, even more preferably between 3 and 25, yet more preferably between 4 and 15. In a further embodiment "b" is between 1 and 150, preferably between 3 and 50, even more preferably between 3 and 25, yet more preferably between 4 and 15. In a further embodiment "c" is between 1 and 150, preferably between 3 and 50, even more preferably between 3 and 25, yet more preferably between 4 and 15.

Depending on the method, it may be desirable for the oligonucleotide to comprise additional labels, quenchers, modified nucleotides or abasic sites. Hence, in one aspect of the present invention the oligonucleotide according to the present invention further comprises additional labels and/or quenchers and/or modified nucleotides and/or non-natural nucleotides and/or abasic sites.

Quenching refers to any process which decreases the fluorescence intensity of a given substance. "Quencher" in context of the present invention relates to a residue which is suited for quenching, e.g. the basic fluorescence of the label without activation. A variety of processes can result in quenching, such as excited state reactions, energy transfer, complex-formation and collisional quenching. As a consequence, quenching is often heavily dependent on pressure and temperature. Molecular oxygen and the iodide ion are common chemical quenchers. Quenching poses a problem for non-instant spectroscopic methods, such as laser-induced fluorescence. Quenching is the basis for Fluorescence Resonance Energy Transfer (FRET) assays. Quenching and dequenching upon interaction with a specific molecular biological target is the basis for activatable optical contrast agents for molecular imaging. There are a few distinct mechanisms by which energy can be transferred non-radiatively: (without absorption or emission of photons) between two dyes, a donor and an acceptor. Förster resonance energy transfer, Dexter energy transfer, Exciplex (excited state complex) formation, and static quenching (also referred to as contact quenching). The skilled artisan is able to choose quenchers according to the needs.

"Modified nucleotides" are known by the skilled artisan. However, in one embodiment of the present invention modified nucleotides are selected from the group consisting of locked nucleic acid (LNA) or peptide nucleic acid (PNA).

An "abasic site" (also known as AP site (apurinic/apyrimidinic site)) in context of the present invention is a location in a nucleic acid/oligonucleotide that has neither a purine nor a pyrimidine base. Abasic sites have been mentioned in "Compositions and Methods for Enhancing Hybridization and Priming Specificity" (US-B1 6,361,940) as well as in "Method for Label-free Detection of Hybridized DNA Target" (US-B1 6,579,680) and "Use of Abasic Site-Containing DNA Strands for Nucleobase Recognition in Water" Yoshimoto et al., JACS Communications, published on Web, Jul. 4, 2003.

The skilled artisan will furthermore recognize that the oligonucleotides according to the present invention may consist of different types of nucleic acids. Hence, in a preferred embodiment the oligonucleotide consists of DNA, RNA, PNA, or LNA.

The oligonucleotide according to the present invention may consist of different length. In one embodiment of the present invention an oligonucleotide has a length of 3 to 300 nucleotides, preferably 5 to 100 nucleotides, more preferably 6 to 50 nucleotides, even more preferably 15 to 30 nucleotides.

It will be acknowledged by those of ordinary skills in the art that the oligonucleotide according to the present invention may serve for different purposes, i.e. primer or hybridization probe. Thus, in one embodiment of the present invention the oligonucleotide according to the present invention is a primer, hybridization probe, a scorpion primer, a scorpion hybridization probe, a TaqMan probe or another functional oligonucleotide as known by the skilled artisan.

However, in a further embodiment the oligonucleotide according to the present invention is a probe. Various kinds of labeled probes are known. These, for example, comprise a quencher and a label. Preferred are TaqMan probes, Scorpion probes, Molecular beacons, light cycler probes, LUX probes, amplifluor probes.

TaqMan probes are hydrolysis probes that are designed to increase the specificity of real-time PCR assays. The TaqMan probe principle relies on the 5'-3' nuclease activity of Taq polymerase to cleave a dual-labeled probe during hybridization to the complementary target sequence and fluorophore-based detection. As in other real-time PCR methods, the resulting fluorescence signal permits quantitative measurements of the accumulation of the product during the exponential stages of the PCR; however, the TaqMan probe significantly increases the specificity of the detection.

Like TaqMan probes, Molecular Beacon probes also use FRET to detect and quantitate the synthesized PCR product via a fluorophore coupled to the 5'-end and a quencher attached to the 3'-end of an oligonucleotide. Unlike TaqMan probes, Molecular Beacon probes are designed to remain intact during the amplification reaction, and must rebind the target in every amplification cycle for signal measurement. Molecular Beacon probes form a stem-loop structure when free in solution. Thus, the close proximity of the fluorophore and quencher prevents the probe from fluorescing. When a Molecular Beacon probe hybridizes to a target, the fluorophore and quencher are separated, FRET does not occur, and the fluorescent dye emits light upon irradiation.

With Scorpion probes, sequence-specific priming and PCR product detection is achieved using a single oligonucleotide. The Scorpion probe maintains a stem-loop configuration in the unhybridized state. The fluorophore is attached to the 5'-end and is quenched by a moiety coupled to the 3' end. The 3' portion of the stem also contains a sequence that is complementary to the extension product of the primer. This sequence is linked to the 5' end of a specific primer via a non-amplifiable monomer. After extension of the Scorpion primer, the specific probe sequence is able to bind to its complement within the extended amplicon thus opening up the hairpin loop. This prevents the fluorescence from being quenched and a signal is observed.

A light cycler FRET probe system is a pair of single-stranded fluorescently-labeled oligonucleotides. Probe 1 (the donor probe) is labeled at its 3'-end with a donor fluorophore (generally fluorescein) and Probe 2 (the acceptor probe) is labeled at its 5'-end with one of four available fluorophores (red 610, 640, 670 or 705). The free 3'-hydroxyl group of Probe 2 must be blocked with a phosphate group (P) to prevent Taq DNA polymerase extension. To avoid any steric problems between the donor and the acceptor fluorophores on both probes, there should be a spacer of 1 to 5 nt (4 to 25 Å distance) to separate the two probes from each other. Before any real-time quantitative PCR reaction takes place, fluorescence background may be observed inside the tube.

Preferably the oligonucleotide is a probe selected from the group of TaqMan probe, Scorpion probe, molecular beacon probe, light cycler probe, LUX probe and amplifluor probe, wherein the probe comprises at least one labeled nucleotide according to the present invention.

Furthermore, it may be desirable to label nucleic acids of different lengths with a labeled nucleotide according to the present invention. Hence, the present invention also relates to a nucleic acid comprising a labeled nucleotide according to the present invention. The nucleic acid according to the present invention may also comprise two or more, three or more, four or more, five or more labeled nucleotides according to the present invention. The labeled nucleotides may be positioned at different positions within said nucleic acid. In one embodiment of the present invention the labeled nucleotide according to the present invention is positioned at the 5'-end of the nucleic acid according to the present invention. In a further embodiment a labeled nucleotide according to the present invention is positioned at the 3'-end of the nucleic acid according to the present invention. In yet a further embodiment a labeled nucleotide according to the present invention is present at an internal position of the nucleic acid according to the present invention.

The present invention furthermore relates to a method for sequencing, or amplifying and detecting nucleic acids comprising the steps of:
i) providing at least one oligonucleotide or nucleic acid primer comprising at least one labeled nucleotide according to the present invention,
ii) providing enzymes and reagents for amplification of a target nucleic acid using said at least one nucleic acid primer,
iii) incubating the components of the reaction under conditions suited for amplification of the target nucleic acid primer,
iv) detecting the amplified nucleic acids via the label of the labeled nucleotide according to the present invention.

In one embodiment the method according to the present invention comprises the step of separating the amplification products according to their lengths. Hence, in one embodiment of the method according to the present invention step iv) comprises a step of separating the amplified nucleic acid according to their lengths, preferably before the detection of the amplified nucleic acids via the labeled nucleotide. The person skilled in the art is aware of a great number of methods to separate nucleic acids according to their length. One commonly used method is gel electrophoresis. Hence, in one embodiment of the present invention the separation of the amplified nucleic acid according to their size is performed using gel electrophoresis. Gel electrophoresis is a technique used for the separation of nucleic acid molecules using an electric field applied to a gel matrix. The term "gel" refers to the matrix used to contain, then separate the target molecules. In most cases, the gel is a crosslinked polymer whose composition and porosity is chosen based on the specific weight/length and composition of the targets to be analyzed. When separating small nucleic acids (DNA, RNA, or oligonucleotides) the gel is usually composed of different concentrations of acrylamide and a cross-linker, producing different sized mesh networks of polyacrylamide. Acrylamide may be for example of the group of acrylamide, linear polyacrylamide, polydimethyl acrylamide or polyisopropyl acrylamide. When separating larger nucleic acids (greater than a few hundred bases), purified agarose may be chosen as the matrix. In both cases, the gel forms a solid, yet porous matrix. Agarose is composed of long unbranched chains of uncharged carbohydrate without cross links resulting in a gel with large pores allowing for the separation of macromolecules and macromolecular complexes. Hence, in one embodiment of the present invention, the matrix used for the separation of the nucleic acids is polyacrylamide or agarose.

Gel electrophoresis is used in forensics, molecular biology, genetics, microbiology and biochemistry. The results can be analyzed quantitatively by visualizing labeled nucleic acids in the gel with an imaging device, usually comprising a light source to excite fluorescence of the labels, e.g. by a laser. The signal from the label is recorded with a detection device, and the intensity of the bands or spots are measured. The measurement and analysis are mostly done with specialized software which transforms the detected signals according to the length of the nucleic acid and the amount of detected nucleic acids into an electropherogram. In a preferred embodiment of the present invention the separation of the amplified nucleic acids is performed by capillary gel electrophoresis.

"Nucleic acid" in the context of the method according to the present invention means a specific class of nucleic acid, inter alia, RNA, DNA, cDNA (complementary DNA), LNA (locked nucleic acid), mRNA (messenger RNA), mtRNA (mitochondrial), rRNA (ribosomal RNA), tRNA (transfer RNA), nRNA (nuclear RNA), siRNA (short interfering RNA), snRNA (small nuclear RNA), snoRNA (small nucleolar RNA), scaRNA (Small Cajal Body specific RNA), microRNA, dsRNA (doubled-stranded RNA), ribozyme, riboswitch, viral RNA, dsDNA (double-stranded DNA), ssDNA (single-stranded DNA), plasmid DNA, cosmid DNA, chromosomal DNA, viral DNA, mtDNA (mitochondrial DNA), nDNA (nuclear DNA), snDNA (small nuclear DNA) or the like or any other class or sub-class of nucleic acid which is distinguishable from the bulk nucleic acid in a sample.

The present invention furthermore relates to a kit comprising a labeled nucleotide according to the present invention. In another embodiment the kit comprises an oligonucleotide according to the present invention. In a further embodiment the kit further comprises a polymerase and optionally dNTPs and/or NTPs and/or ddNTPs. The kit may also comprise buffer and reagents for the amplification of nucleic acids.

The oligonucleotide according to the present invention may be used as a nucleic acid probe or as a primer in nucleic acid amplification methods.

However, the inventors found that the oligonucleotide according to the present invention confers a higher stability to the oligonucleotide itself as well as to the amplification products. Hence, in a preferred embodiment the oligonucleotide according to the present invention is a primer for a nucleic acid amplification method. In a preferred embodiment the present invention relates to the use of an oligonucleotide according to the present invention in a method selected from the group consisting of polymerase chain reaction (PCR), ligase chain reaction (LCR), transcription-based amplification system (TAS), nucleic acid sequence based amplification (NASBA), rolling circle amplification (RCA), transcription-mediated amplification (TMA), self-sustaining sequence replication (3 SR) and Qβ amplification, strand displacement amplification (SDA), multiple displacement amplification (MDA), loop-mediated isothermal amplification (LAMP), helicase-dependent Amplification (HDA), smart-amplification process (SMAP), quantitative real-time PCR (qPCR), reverse-transcriptase PCR (RT-PCR).

EXAMPLES

Example 1

The PCR was carried out as follows:

0.2 µl Multi Taq2 DNA Polymerase (QIAGEN, Hilden, Germany) was used as Hot-start DNA polymerase. 2.5 µl Reaction MixB (QIAGEN, Hilden, Germany) was used as a PCR buffering solution.

0.4 µM labeled forward primer TH01-P-2×C3 (5'-DY530-C6-C3-C3-gtgattcccattggcctgttc-3'; SEQ ID NO. 1) or 0.4 µM labeled forward primer TH01-P-DY530 (5'-DY530-C6-gtgatteccattggcagttc-3'; SEQ ID NO. 2) in combination with 0.4 µM unlabeled TH01_rev reverse primer (5'-attcctgtgggct-gaaaagctc-3'; SEQ ID NO. 3), all produced by Biomers.net (Ulm, Germany), were used for PCR amplification. The volume of 25 µl was completed by Nuclease-free water (QIAGEN, Hilden, Germany). PCR was carried out using an thermocycler 9700 PCR System Gold (Life Technologies Corporation, Carlsbad, Calif., USA) with the following protocol.

TABLE 1

Primers

| SEQ ID NO. | Name | Sequence | Information |
|---|---|---|---|
| 1 | TH01-P-2 × C3 (labeled forward primer comprising a linker) | 5'-DY530-$C_6$-$C_3$-$C_3$-gtgattcccattggcctgttc-3' | X is DY530; SP is a $C_6$-aminolinker; n is 1; $R^1$ is a phosphate group; $R^2$, $R^3$ and $R^4$ are each $H_2$, "a" is 2, and Y is the 5'-carbon of the sugar of the guanine at position 1 of the oligonucleotide |

TABLE 1-continued

Primers

| SEQ ID NO. | Name | Sequence | Information |
|---|---|---|---|
| 2 | TH01-P-DY530 (labeled forward primer) | 5'-DY530-C$_6$-gtgattcccattggcctgttc-3' | standard PCR primer labeled to DY530 with a standard C$_6$-aminolinker |
| 3 | TH01_rev (unlabeled reverse primer) | 5'-attcctgtgggctgaaaagctc-3' | |
| 4 | TH01-P-3 × C3 (labeled forward primer comprising a linker) | 5'-DY530-C$_6$-C$_3$-C$_3$-C$_3$-gtgattcccattggcctgttc-3' | X is DY530; SP is a C$_6$-aminolinker; "n" is 1; R$^1$ is a phosphate group; R$^2$, R$^3$ and R$^4$ are each H$_2$, "a" is 3, and Y is the 5'-carbon of the sugar of the guanine at position 1 of the oligonucleotide |

TABLE 2

Cycling conditions

| Temperature | Time | |
|---|---|---|
| 96° C. | 2 min | |
| 94° C. | 30 s | ⎫ |
| 59° C. | 120 s | ⎬ 30 cycles |
| 72° C. | 90 s | ⎭ |
| 60° C. | 45 min | |
| 4° C. | ∞ | |

1 μl of cycled PCR probes were added to 12 μl Hi-Di Formamide (Life Technologies Corporation, Carlsbad, Calif., USA) and 0.5 μl DNA size standard 550 (BTO) (QIAGEN, Hilden, Germany) and incubated for 3 min at 95° C.

The denatured PCR probes were analyzed by capillary electrophoresis using a 3500 Genetic Analyzer (Life Technologies Corporation, Carlsbad, Calif., USA) under standard conditions. Results are shown in FIG. 1.

These results clearly demonstrate that the use of labeled primers comprising a labeled nucleotide according to the present invention, i.e. with a linker according to the present invention, result in a reduction of artificial unwanted peaks. In these examples the baseline in the crucial range of 130 to 550 bp is absolutely clean by using C3 modified PCR primers. Beside this range the artificial unwanted peaks are significantly reduced in height and amount. In contrast, standard PCR primers that are labeled at the 5' end, cause numerous artificial peaks with up to 110 relative fluorescence units (rfu). PCR amplifications with minimal amounts of template DNA result typically in PCR products giving peaks of around 200 rfu. Using standard labeled primers the interpretation of electropherograms is impaired by numerous, high, artificial peaks (dye blobs), which results in an incomplete appraisement of the probe. Using linker modified primers, PCR products of 200 rfu can be clearly distinguished from dyeblobs particularly in the range between 130 and 550 bp. These benefits give a huge advantage in the sensitivity of the method.

Example 2

Figure 2:
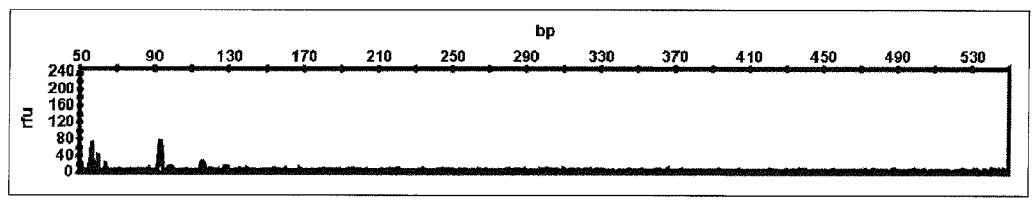

When using primers that are modified by a linker comprising two repeats of a C$_3$ linker ("n" is 1 and "a" is 3) a strong reduction of background noise is apparent, supra. However, in further experiments different numbers of linker repeats attached to the labeled primer were analyzed. In one example a primer comprising a labeled nucleotide according to the present invention at its 5'-position, comprising three sequential C$_3$-repeats; i.e. "a" is 3 (TH01-P-3×C3: 5'-DY530-C6-C3-C3-C3-gtgattcccattggcctgttc-3'; SEQ ID NO. 4) together with the unlabeled reverse primer TH01_rev (5'-attcct-gtgggctgaaaagctc-3'; SEQ ID NO. 3) was analyzed by the method described above. Results are shown in FIG. 2.

These results demonstrate that a primer comprising a labeled nucleotide according to the present invention comprising three C$_3$-repeats also results in a reduction of background noise. In comparison to standard labeled primers (see FIG. 1) the baseline in the crucial range of 130 to 550 bp is absolutely clean. Moreover, also beside this range the artificial unwanted peaks are significantly reduced in height and amount by using the primer comprising a labeled nucleotide according to the present invention.

Figure Legend

FIG. 1: Effect of labeled nucleotides according to the present invention. A PCR without template DNA was performed with each 0.4 μM forward and reverse primer. The PCR probes were analyzed by capillary electrophoresis afterwards. In (A) the result of the no-template-control (NTC) PCR with a standard labeled primer is shown. The result of the NTC-PCR using the specific labeled primer (SEQ ID NO. 1, i.e. comprising a labeled nucleotide according to the present invention, is shown in (B). The primer comprising a labeled nucleotide according to the present invention reduces significantly the amount and height of unwanted artificial peaks. In the crucial range between 130 and 550 bp the baseline is absolutely flat.

FIG. 2: A PCR without template DNA was performed with each 0.4 μM forward and reverse primer. The PCR probe was analyzed by capillary electrophoresis afterwards. The result of the no-template-control (NTC) PCR using a labeled primer comprising a labeled nucleotide according to present invention (SEQ ID NO. 4) is shown. The C3 modified primer reduces significantly the amount and height of unwanted artificial peaks. In the range between 130 and 550 bp the baseline is absolutely flat.

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: labelled forward primer comprising a linker
<220> FEATURE:
<221> NAME/KEY: misc_binding
<222> LOCATION: (1)..(1)
<223> OTHER INFORMATION: guanin is linked to DY530 label through a
      linker, the linker is having the formula as set out in Formula 1,
      wherein X is DY530, SP is a C6-aminolinker, n is 1, R1 is a
      phosphate group, R3 and R4 are each H2, "a" is 2 and Y is the
      5'carbon of the guanine

<400> SEQUENCE: 1
gtgattccca ttggcctgtt c                                              21

<210> SEQ ID NO 2
<211> LENGTH: 21
<212> TYPE: DNA
<213> ORGANISM: Artificial Sequence
<220> FEATURE:
<223> OTHER INFORMATION: labelled forward primer
<220> FEATURE:
<221> NAME/KEY: misc_binding
<222> LOCATION: (1)..(1)
<223> OTHER INFORMATION: guanin is bound to DY530 through a
      C6-aminolinker

<400> SEQUENCE: 2
gtgattccca ttggcctgtt c                                              21

<210> SEQ ID NO 3
<211> LENGTH: 22
<212> TYPE: DNA
<213> ORGANISM: Artificial Sequence
<220> FEATURE:
<223> OTHER INFORMATION: unlabelled reverse primer

<400> SEQUENCE: 3
attcctgtgg gctgaaaagc tc                                             22

<210> SEQ ID NO 4
<211> LENGTH: 21
<212> TYPE: DNA
<213> ORGANISM: Artificial Sequence
<220> FEATURE:
<223> OTHER INFORMATION: labelled forward primer comprising a linker
<220> FEATURE:
<221> NAME/KEY: misc_binding
<222> LOCATION: (1)..(1)
<223> OTHER INFORMATION: guanin is linked to DY530 label through a
      linker, the linker is having the formula as set out in Formula 1,
      wherein X is DY530, SP is a C6-aminolinker, n is 1, R1 is a
      phosphate group, R3 and R4 are each H2, "a" is 3 and Y is the
      5'carbon of the guanine

<400> SEQUENCE: 4
gtgattccca ttggcctgtt c                                              21

The invention claimed is:

1. A labeled nucleotide comprising a label attached via a linker, wherein the labeled nucleotide has the formula

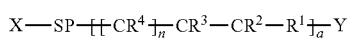  Formula 1 wherein $R^1$ is a residue selected from the group consisting of a phosphate group, and a sulphate group;
wherein $R^2$, $R^3$ and $R^4$ are independently selected from the group consisting of $H_2$, $OH_2$, and O;
wherein "n" is an integer between 1 and 16;
wherein "a" is an integer between 2 and 10;
wherein SP is absent or a spacer;
wherein X is said label; and
wherein Y is a nucleotide or nucleoside.

2. The labeled nucleotide according to claim 1, wherein $R^1$ is a phosphate group.

3. The labeled nucleotide according to claim 1, wherein $R^2$, $R^3$, and $R^4$ are each $H_2$.

4. The labeled nucleotide according to claim 1, wherein n is 1, wherein $R^2$, $R^3$ and $R^4$ are each $H_2$, and wherein $R^1$ is a phosphate group, and wherein "a" is 2.

5. The labeled nucleotide according to claim 1, wherein X is selected from the group of labels consisting of 5- or 6-carboxyfluorescein (FAM™), VIC™, NED™,fluorescein, fluorescein isothiocyanate (FITC), IRD-700/800, cyanine dyes, such as CY3™, CY5™, CY3.5™, CY5.5™, Cy7™, xanthen, 6-carboxy-2',4',7',4,7-hexachlorofluorescein (HEX), 6-carboxy-1,4-dichloro-2',7'-dichloro-fluorescein (TET®), 6-carboxy-4',5'-dichloro-2',7'-dimethodyfluorescein (JOE™), N,N,N',N'-tetramethyl-6-carboxyrhodamine (TAMRA™), 6-carboxy-X-rhodamine (ROX), 5-carboxyrhodamine-6G (R6G5), 6-carboxyrhodamine-6G (RG6), rhodamine, rhodamine green, rhodamine red, rhodamine 110, Rhodamin 6G®, BODIPY dyes, such as BODIPY TMR, oregon green, coumarines, such as umbelliferone, benzimides, such as Hoechst 33258; phenanthridines, such as Texas Red®, California Red®, Yakima Yellow, Alexa Fluor® 350, Alexa Fluor® 405, Alexa Fluor® 430, Alexa Fluor® 488, Alexa Fluor® 500, Alexa Fluor® 514, Alexa Fluor®532, Alexa Fluor® 546, Alexa Fluor® 555, Alexa Fluor® 568, Alexa Fluor® 594, Alexa Fluor® 610, Alexa Fluor® 633, Alexa Fluor® 647, Alexa Fluor® 660, Alexa Fluor® 680, Alexa Fluor® 700, Alexa Fluor® 750, PET®, ethidium bromide, acridinium dyes, carbazol dyes, phenoxazine dyes, porphyrine dyes, polymethin dyes, Atto 390, Atto 425, Atto 465, Atto 488, Atto 495, Atto 520, Atto 532, Atto 550, Atto 565, Atto 590, Atto 594, Atto 620, Atto 633, Atto 647N, Atto 655, Atto RhoG6, Atto Rho11, Atto Rho12, Atto Rho101, BMN™-5, CEQ8000 D2, CEQ8000 D3, CEQ8000 D4, DY-480XL, DY-485XL, DY-495, DY-505, DY-510XL, DY-521XL, DY-521XL, DY-530, DY-547, DY-550, DY-555, DY-610, DY-615, DY-630, DY-631, DY-633, DY-635, DY-647, DY-651, DY-675, DY-676, DY-680, DY-681, DY-700, DY-701, DY-730, DY-731, DY-732, DY-750, DY-751, DY-776, DY-780, DY-781, DY-782, 6-carboxy-4',5'-dichloro-2',7'-dimethoxyfluorescein (JOE), TET™, CAL Fluor® Gold 540, CAL Fluor RED 590, CAL Fluor Red 610, CAL Fluor Red 635, IRDye® 700Dx, IRDye® 800CW, Marina Blue®, Pacific Blue®, Yakima Yellow®, 6-(4,7-Dichloro-2',7'-diphenyl-3',6'-dipivaloylfluorescein-6-carboxamido)-hexyl-1-O-(2-cyanoethyl)-(N,N-diisopropyl)-phosphoramidite (SIMA), CAL, Fluor® Gold 540, CAL Fluor® Orange 560, CAL Fluor Red 635, Quasar 570, Quasar 670, LIZ, Sunnyvale Red, LC Red® 610, LC Red® 640, LC Red®670, and LC Red® 705.

6. The labeled nucleotide according to claim 1 wherein Y is selected from the group consisting of ribose nucleotides, 2'-deoxyribose nucleotides, 2',3'-di-deoxy-ribose nucleotides, mono-phosphate nucleosides, di-phosphate nucleosides and tri-phosphate nucleosides.

7. The :labeled nucleotide according to claim 1, wherein y is selected from the group consisting of adenine nucleotides, thymidine nucleotides, cytosine nucleotides, guanine nucleotides, uridine nucleotides, 7-methyl-guanine nucleotides, 5-methyl-cytosine nucleotides, inosine nucleotides , hypoxanthine, xanthine, 7-Methylguanine, inosine, xanthinosine, 7-methylguanosine, 5,6-dihydrouracil, 5-methyleytosine, pseudouridine, dihydrouridine, and 5-methylcytidine, and derivatives thereof.

8. The labeled nucleotide according to claim 1 further comprising a protecting group.

9. An oligonucleotide comprising at least one labeled nucleotide according to claim 1.

10. The oligonucleotide according to claim 9, wherein said at least one labeled nucleotide is at the 5'-end of the oligonucleotide or at the 3'-end of the oligonucleotide.

11. The oligonucleotide according to claim 9, wherein said at least one labeled nucleotide is at an internal position of the oligonucleotide.

12. A kit comprising an oligonucleotide according to claim 9.

13. A method for amplifying and detecting a target nucleic acid comprising:
i) providing at least one nucleic acid primer comprising at least one labeled nucleotide according to claim 1,
ii) providing enzymes and reagents for amplification of the target nucleic acid using said at least one nucleic acid primer,
iii) incubating the components of the reaction under conditions suited for amplification of the target nucleic acid thereby forming amplified nucleic acid, and
iv) detecting the amplified nucleic acid via the label of the labeled nucleotide.

14. The method according to claim 13, wherein the detecting in iv) comprises separating the amplified nucleic acid according to length.

15. The labeled nucleotide according to claim 1, wherein n is 1.

16. The labeled nucleotide according to claim 15, wherein "a" is 2.

17. The labeled nucleotide according to claim 16, wherein X is selected from the group consisting of FAM™, DY-510, DY-530, and Atto 550.

18. The labeled nucleotide according to claim 17, wherein SP is a spacer attached to $CR^4$ via a phosphate group.

19. The labeled nucleotide according to claim 18, wherein SP comprises a $C_5$- or $C_6$-ammolinker.

20. The labeled nucleotide according to claim 1, wherein n is 1, "a" is 2, SP comprises a $C_5$ or $C_6$-aminolinker attached to $CR^4$ via a phosphate group, and X is DY-530.

* * * * *